United States Patent [19]
Masumoto

[11] Patent Number: 6,076,196
[45] Date of Patent: Jun. 20, 2000

[54] GOGGLES HAVING STRAP BEARING ARMS CONNECTED TO A GOGGLE FRAME BETWEEN CENTRAL AND LATERAL END PORTIONS THEREOF

[75] Inventor: Yuusuke Masumoto, Higashiosaka, Japan

[73] Assignee: Yamamoto Kogaku Co., Ltd., Osaka, Japan

[21] Appl. No.: 09/025,934

[22] Filed: Feb. 19, 1998

[30] Foreign Application Priority Data

Feb. 19, 1997 [JP] Japan ................................. 9-034746

[51] Int. Cl.[7] ..................................................... A61F 9/02
[52] U.S. Cl. ............................ 2/436; 2/425; 2/439; 2/452
[58] Field of Search ............................... 2/436, 437, 439, 2/440, 450, 452, 426, 424, 425

[56] References Cited

U.S. PATENT DOCUMENTS

| | | | |
|---|---|---|---|
| 4,435,852 | 3/1984 | Nesler | 2/436 |
| 4,977,627 | 12/1990 | Metcalfe et al. | 2/437 |
| 5,734,995 | 4/1998 | Chiang | 2/452 X |
| 5,829,064 | 11/1998 | Huang | 2/452 X |

*Primary Examiner*—Peter Nerbun
*Attorney, Agent, or Firm*—Koda & Androlia

[57] ABSTRACT

A pair of goggles include a frame with an upper frame portion and a lower frame portion, arms extruded from extrusion positions on the upper and lower frame portions, and a strap being attached to the arms. The frame and arms are integrally made of soft elastic synthetic resin. The strap is attached to the arms at strap attaching positions at their distal end portions away from the extrusion positions. The arms are formed in a manner that the arms overlap with at least part of a front surface of said frame or that the arms extend in front of and generally along the front surface of the frame.

12 Claims, 15 Drawing Sheets us 6,076,196

GOGGLES HAVING STRAP BEARING ARMS CONNECTED TO A GOGGLE FRAME BETWEEN CENTRAL AND LATERAL END PORTIONS THEREOF

BACKGROUND OF THE INVENTION

1. Field of the Invention

The present invention relates to a pair of goggles to be used for various sports and work requiring helmets such as ski races.

2. Prior Art

At present, in a variety of ski races, whether or not goggles are required is mainly dependent on the sliding speed.

One type of goggles which are used on a helmet requires a specific design which is different from that of goggles which are worn directly on a wearer's head. This is because, when goggles are put on a helmet, the thickness of the interior or the shell of the helmet causes an acting direction of the tension of the strap on the goggles to change, which, as a result, causes an uncomfortable fitness of the goggles on the wearer's face and allows wind and snow to intrude into a gap between goggles and the wearer's face.

Referring concretely to FIG. 14, conventional goggles designed to be used together with a helmet usually have a large width (i.e. they are wide in lateral directions as seen from the front) and a large thickness. This is because the frame of such goggles is designed to accord with the thickness of an associated helmet. When these goggles are put directly on a wearer's head, due to the large width in the lateral directions, the comfort level of these goggles on the wearer's face is interior to known goggles which are not designed to be used on a helmet. In FIGS. 14 and 15, references 90, G, R, M and S respectively denote a strap, goggles, an interior liner, a wearer's head and a helmet shell. Arrows denote the directions toward which forces are applied.

On the other hand, when conventional goggles designed not to be used with a helmet are put on a helmet, due to the tension of the strap, the goggles are likely to be forced to rise and separate from a wearer's face. This is because the frame of such goggles has a small thickness at both sides, there is a difference between the level of the surface of the helmet and that of the wearer's face, and therefore the coupling positions of the strap and the frame are separated up from the face level toward the level of the surface of the helmet, in other word, the coupling positions come to be suspended between the two levels. There is another type of goggles as shown in FIG. 15. Such goggles have additional parts P by which the coupling positions of the strap and the goggle frame are brought close to the surface of the helmet. However, this provides little actual effect on the tension of the strap and thereby ending up with a trifle effect on the fit of goggles.

Therefore nervous athletes who are prone to be affected by the fitting condition and function of goggles must prepare different types of goggles in order to participate in several kinds of races.

Although goggles for skiing are described above, other kinds of goggles for various sports, such as motocross, or for work also require comfortable fit and the same problems stated above must be solved.

SUMMARY OF THE INVENTION

It is hence an object of the present invention to provide a pair of goggles which provide comfortable fit on a wearer's face in spite of the thickness of the interior liner of a helmet or whether the goggles are in use with a helmet or not.

The goggles according to the present invention include a frame and arms formed integrally of soft elastic synthetic resin. The arms respectively extrude from protruded positions on left and right sides of an upper and a lower portion of the frame. Each of the arms has its distal end in the vicinity of a strap fixing position away from the protruded positions and is connected with a strap via a strap fixing means at the vicinity of its distal end. The arm is overlapped with at least part of a front surface of the frame or disposed in front of and generally along the front surface.

The goggles according to the present invention may include a lens holding frame and arms formed integrally of soft elastic synthetic resin. The arms extrude from their respective protrusion positions on left and right sides of the surfaces of an upper and a lower frame portion of the frame. Each of the arms has its distal end in the vicinity of a strap fixing position distanced from its protrusion positions and is connected with a strap via a strap fixing means at the vicinity of its distal end. The arm is overlapped with the upper and lower front surfaces of the lens holding frame or disposed generally along these front surfaces.

The goggles according to the present invention may further include an arm bridging part which connects the upper and lower parts of the arm in the vicinity of its distal ends and the arm bridging part is formed in a shape substantially corresponding to a configuration of a front surface of the side portion of the frame.

In the goggles of the present invention, it is preferable to leave a 2 to 8 cm distance between one of the protruding positions and the center of the lens holding frame.

The above and other objects, features and advantages of the present invention will become apparent from the following description in conjunction with the accompanying drawings.

DETAILED DESCRIPTION OF PREFERRED EMBODIMENTS

Embodiments according to the present invention will be detailed below with reference to the drawings.

Figure 1:
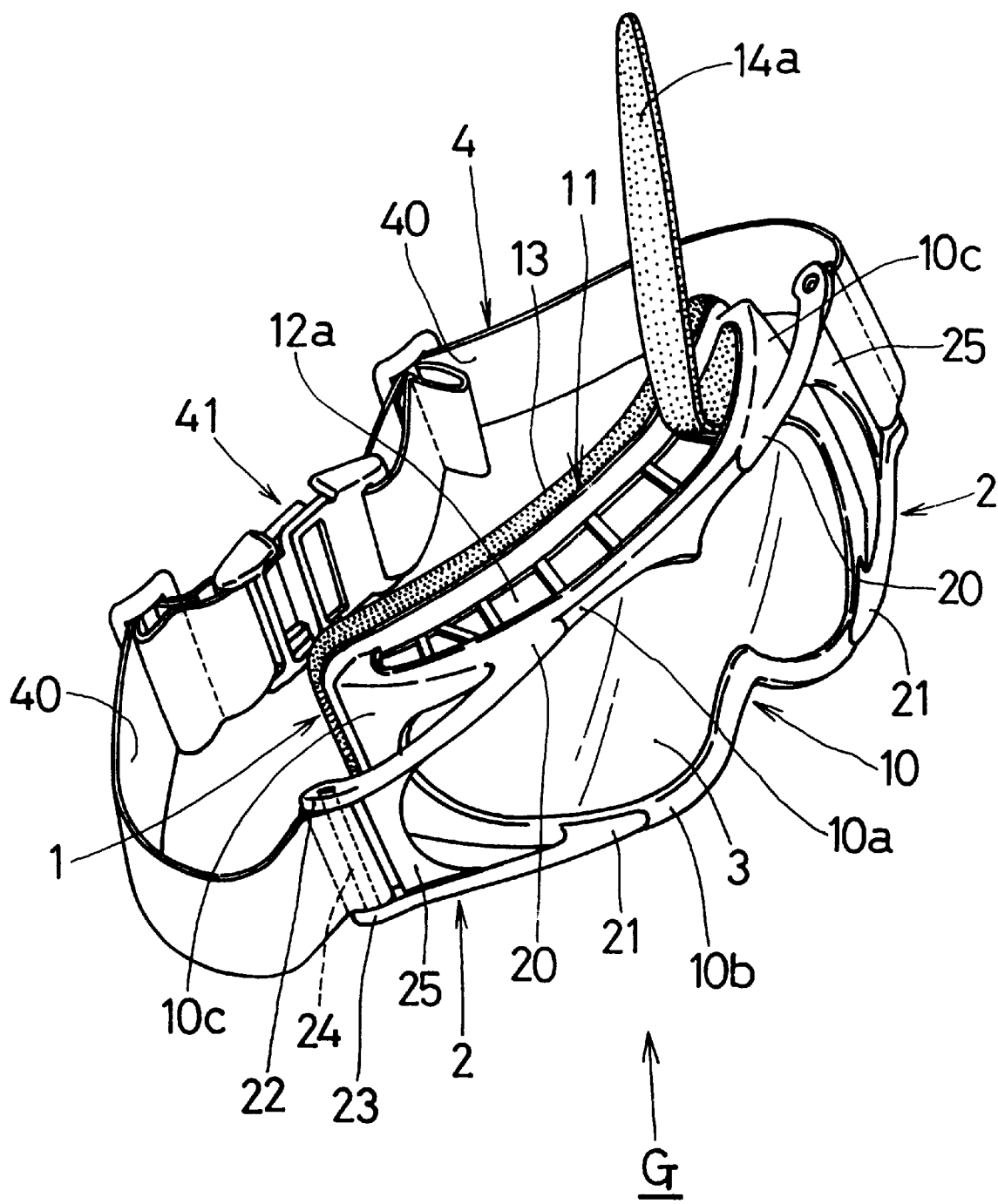
FIG. 1 is a perspective view of a pair of goggles according to one embodiment of the present invention.

An embodiment of a pair of goggles for skiing according to the present invention is shown in FIG. 1. A sponge strip 14a is bent up in the drawing. The goggles include the following basic elements: a frame 1, arms 2, a lens 3, and a flexible strap 4.

The respective elements of the goggles are described in detail below.

Figure 2:
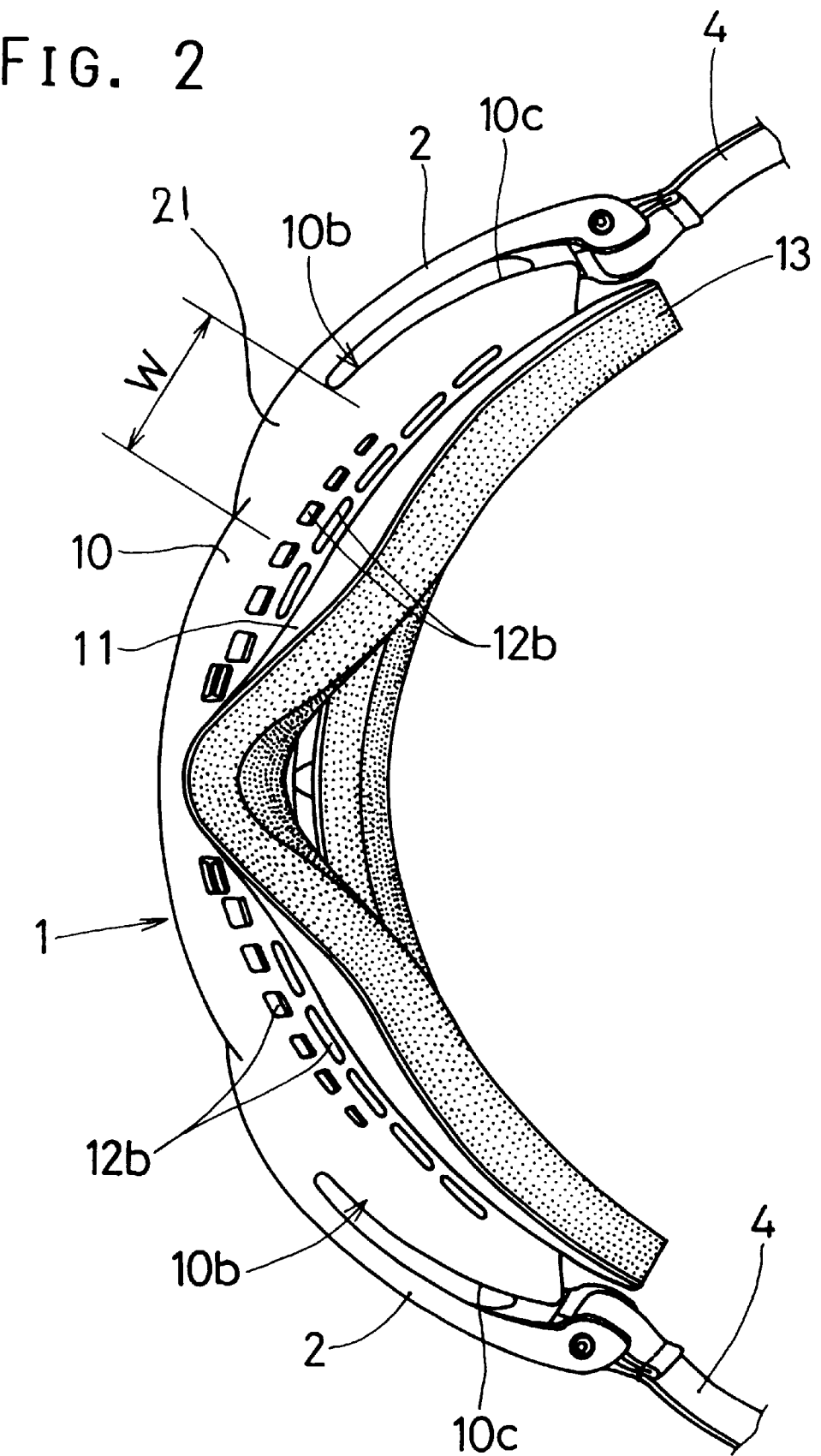
FIG. 2 is a bottom view of the goggles in FIG. 1.
Figure 3:
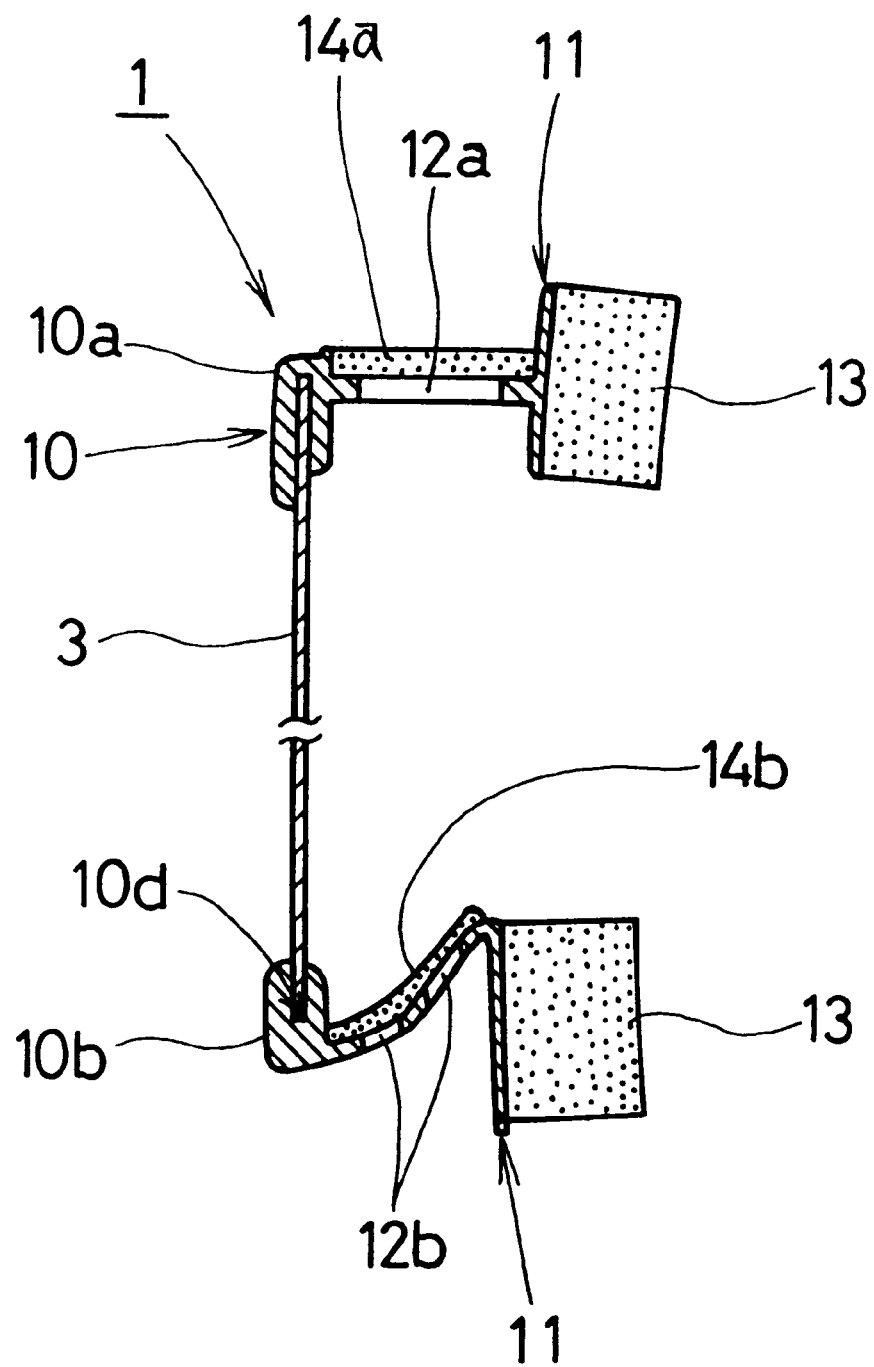
FIG. 3 is a vertical cross section of the goggles in FIG.1.

As shown in FIGS. 1 to 3, the frame 1 includes a lens holding frame 10 disposed in front, a base plate 11 which is disposed behind the lens holding frame 10, and a thick sponge pad 13 which is pasted to the base plate 11. The frame 1 further includes ventilation parts 12a and 12b between the lens holding frame 10 and the base plate 11. The entire frame 1 is made of flexible vinyl chloride (any other soft elastic synthetic resins can be used) and gradually becomes thinner from the center towards both sides. As an alternative, the sponge pad 13 may be attached directly on the rear side of the lens holding frame 10.

The lens holding frame 10 has in its inner circumference a fitting groove 10d in which the lens 3 is fitted and held, as shown in FIG. 3. Other means, although not further described, which prevent an inadvertent removal of the lens 3 can be employed.

The base plate 11 is provided in order to enlarge a contact area between a wearer's face and the frame 1 via the sponge pad 13, and is shaped in a strap plate (a width of about 15 to 20 mm) corresponding to the configuration of the lens holding frame 10.

The ventilation parts 12a and 12b provided respectively on an upper frame portion 10a and on a lower frame portion 10b have entirely different constitutions. To put it concretely, the ventilation part 12a on the upper frame portion has, as shown in FIG. 1, a space portion in a crescent overall shape between the lens holding frame 10 and the base plate 11, and the crescent-shaped space portion is divided into spaces by connection bars. The connection bars flexibly maintain the distance and the positional relationship between the lens holding frame 10 and the base plate 11, and a flexible deformation of the bars also absorbs the shock against the lens holding frame 10 to some extent. On the other hand, the ventilation part 12b on the lower frame portion has two rows of holes as shown in FIG. 2. These ventilation parts 12a and 12b can be covered with thin sponge strips 14a and 14b, as shown in FIG. 3, so as to prevent substances except air, such as snow and dust, from intruding inside the goggles.

Figure 4:
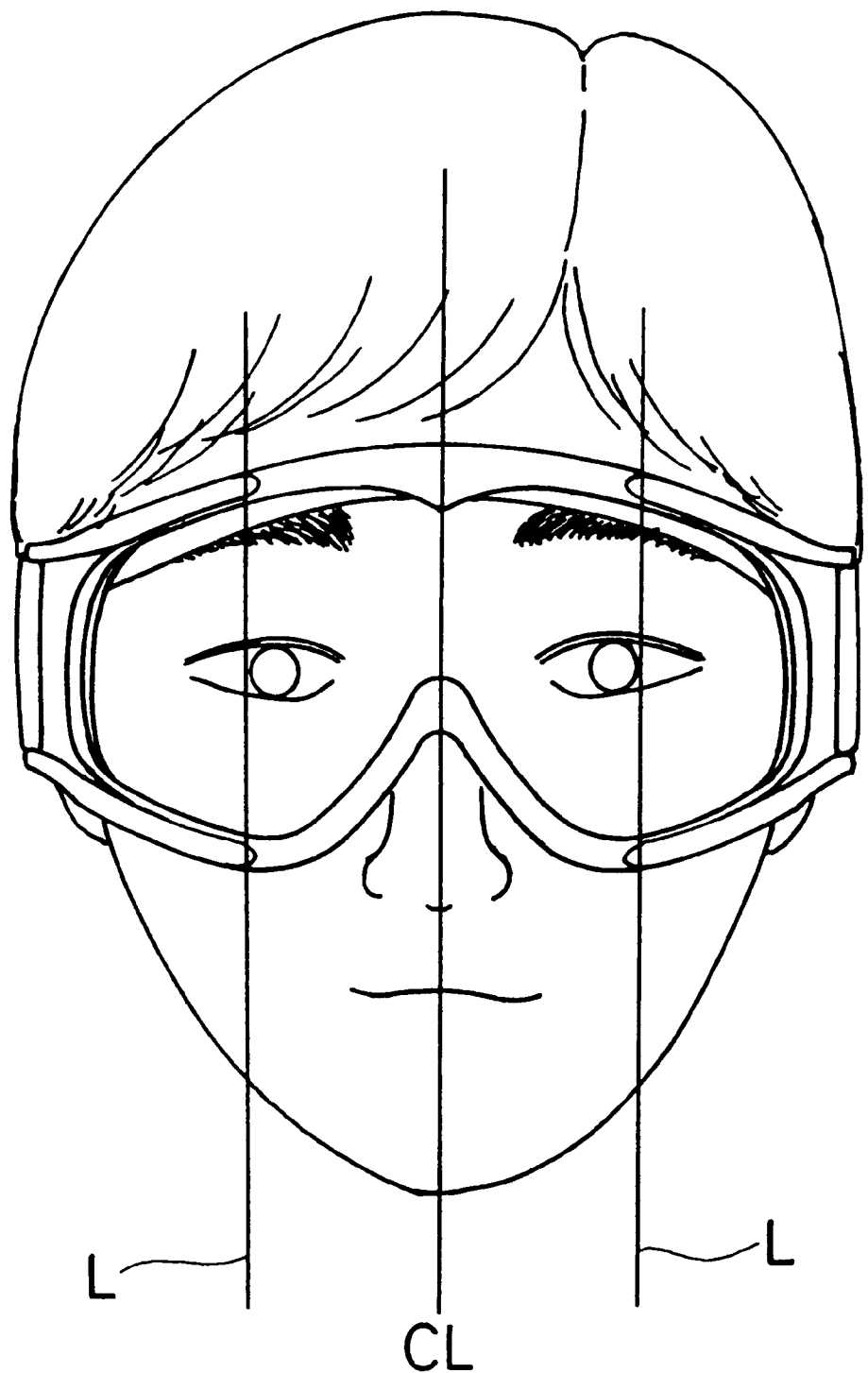
FIG. 4 is a view showing positions from which arms protrude out of a frame of the goggles in FIG. 1.

The arms 2 are made of elastic synthetic resin such as soft vinyl chloride and integrally formed with the frame 1. As shown in FIGS. 1 and 2, the arms 2 are constituted to correspond to the configuration of the right and left sides of the front surface of the lens holding frame 10. One end 20 of each arm 2 protrudes out of the front surface of the upper frame portion 10a of the lens holding frame 10, whereas the other end 21 protrudes from that of the lower frame portion 10b. The arm is arranged to extend generally along the front surfaces of the upper and lower frame portions 10a and 10b of the lens holding frame 10 when the goggles are not in use, and not to intervene the front view defined by the lens holding frame 10. As shown in FIGS. 2 and 4, the extrusion position of the end 21 (it holds true on the end 20) is at the middle point of the width W of the connecting portion to the lens holding frame 10, and on vertical lines L corresponding to a wearer's eyes when in use. The position may not be limited strictly to as FIG. 4 but may be either closer to or farther from the center line CL. It is preferable that the distance between the protrusion position of the arm 2 and the middle point of the frame 10 is within the range of 2 to 8 cm. The reason for this is if the protrusion position is too far from the middle point of the lens holding frame 10, the overall comfort level of goggles deteriorates, while if the protrusion position is too close to the middle point, not only is there a lack of comfort but also the arms are obliged to be lengthened, resulting in an increase of weight of the goggles.

The arms 2 are respectively provided with fitting portions to an elastic strap 4 on the respective distal end portions. As shown in FIG. 1, the elastic strap 4 is fixed with arms 2 in a manner that cylindrical end portions of the straps 4 surround stems 24 bridged between the upper and lower distal end portions 22 and 23.

Each of the arms 2 includes an upper part, a lower part and a bridging part 25 which connects the upper and lower parts together at the distal end portion sides. The bridging part 25 has a configuration corresponding to that of an associated side of the front surface of the frame.

The lens 3 is made of an acrylic resin plate which has a high resistance to scratches and can shield ultraviolet rays almost perfectly.

The elastic strap 4 includes elastic belts 40 and a buckle 41. The elastic belts 40, which are per se constructed elastic and fixed to the arms 2, are held together by means of the buckle 41.

Now comfort of the goggle on a wearer's face is described.

Figure 5:
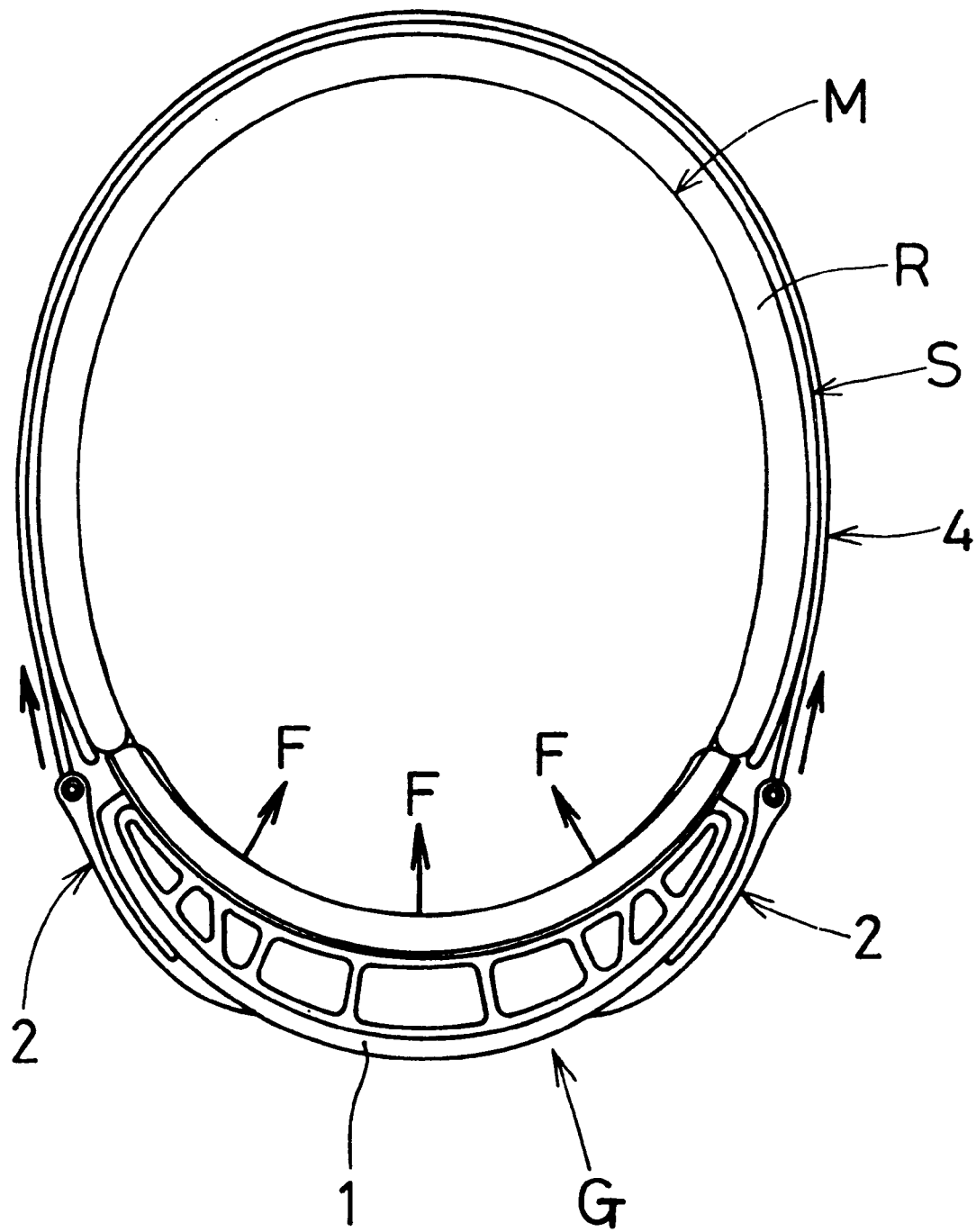
FIG. 5 is a cross section showing a state where the goggles are put on a helmet with a thin interior liner.

FIG. 5 shows a state where the goggles G are put on a helmet with a thin interior liner R. References M and S in FIGS. 5 to 8 respectively denote a wearer's head and a helmet shell.

In FIG. 5, the arms 2 are deformed close to the front surfaces of the upper and lower frame portions 10a and 10b, and to the front surfaces of the side frame portions 10c of the frame 1. Herein the elastic restoring force of the elastic strap 4 is converted into the pressure F of the goggles G against the wearer's face. Therefore, when the goggles G are used with this type of helmet, a force will not be exerted on the goggles to rise and separate from the wearer's face.

Since the frame 1 of the goggles G are designed to gradually become thinner towards both sides from the center a wide field of vision can be secured.

Figure 6:
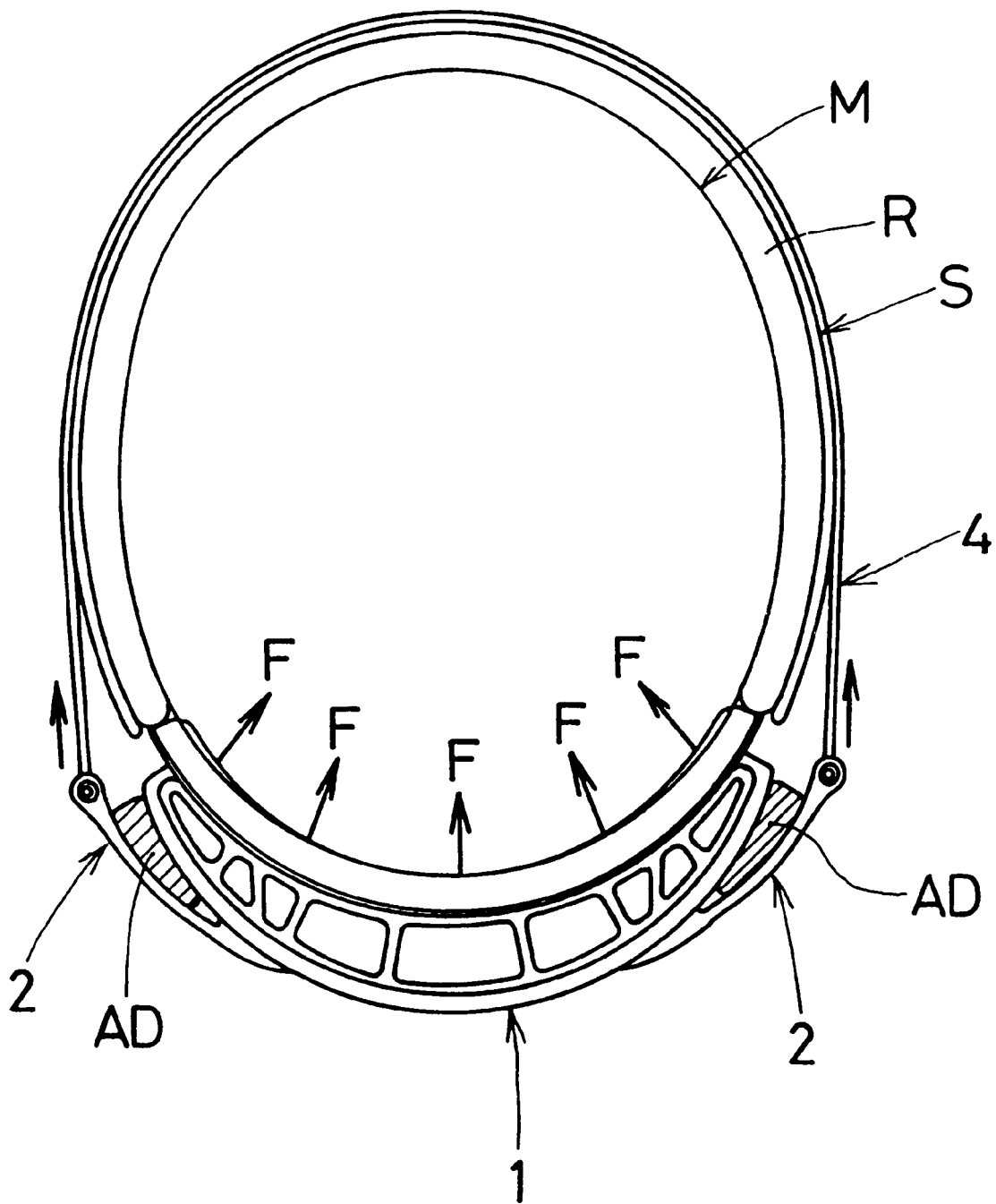
FIG. 6 is a cross section showing a state where adapters are provided between the frame and the arms of the goggles in FIG. 5.

In case a stronger pressure on both sides of a wearer's face with this type of goggles G is required, as shown in FIG. 6, adapters AD can be additionally provided between the frame 1 and the arms 2 so that a desired comfort level can be obtained.

Figure 7:
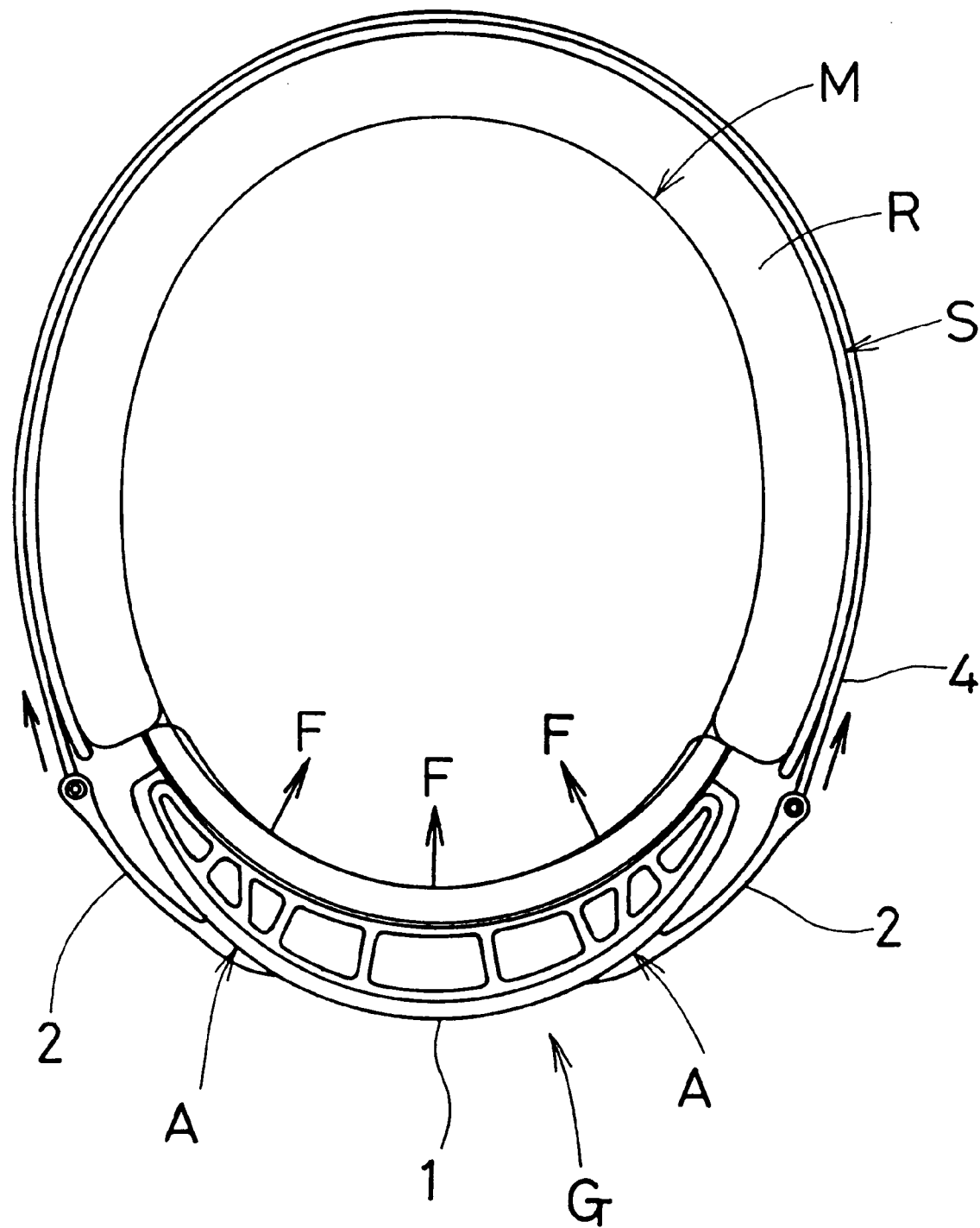
FIG. 7 is a cross section showing a state where the goggles are put on a helmet with a thick interior liner.

FIG. 7 shows a state where the goggles G are put on a helmet with a thick interior liner R.

In this case, the respective arms 2 flexibly deform using points A in the lens holding frame 10 as their fulcrums. Since the tension of the strap which acts on the arms 2 is applied on the points A, the elastic restoring force of the elastic strap 4 is directly converted into a pressure F against a wearer's face. Therefore, when the goggles G are used on such a thick helmet, a force will not be exerted on the goggles to rise and separate from the wearer's face.

Figure 8:
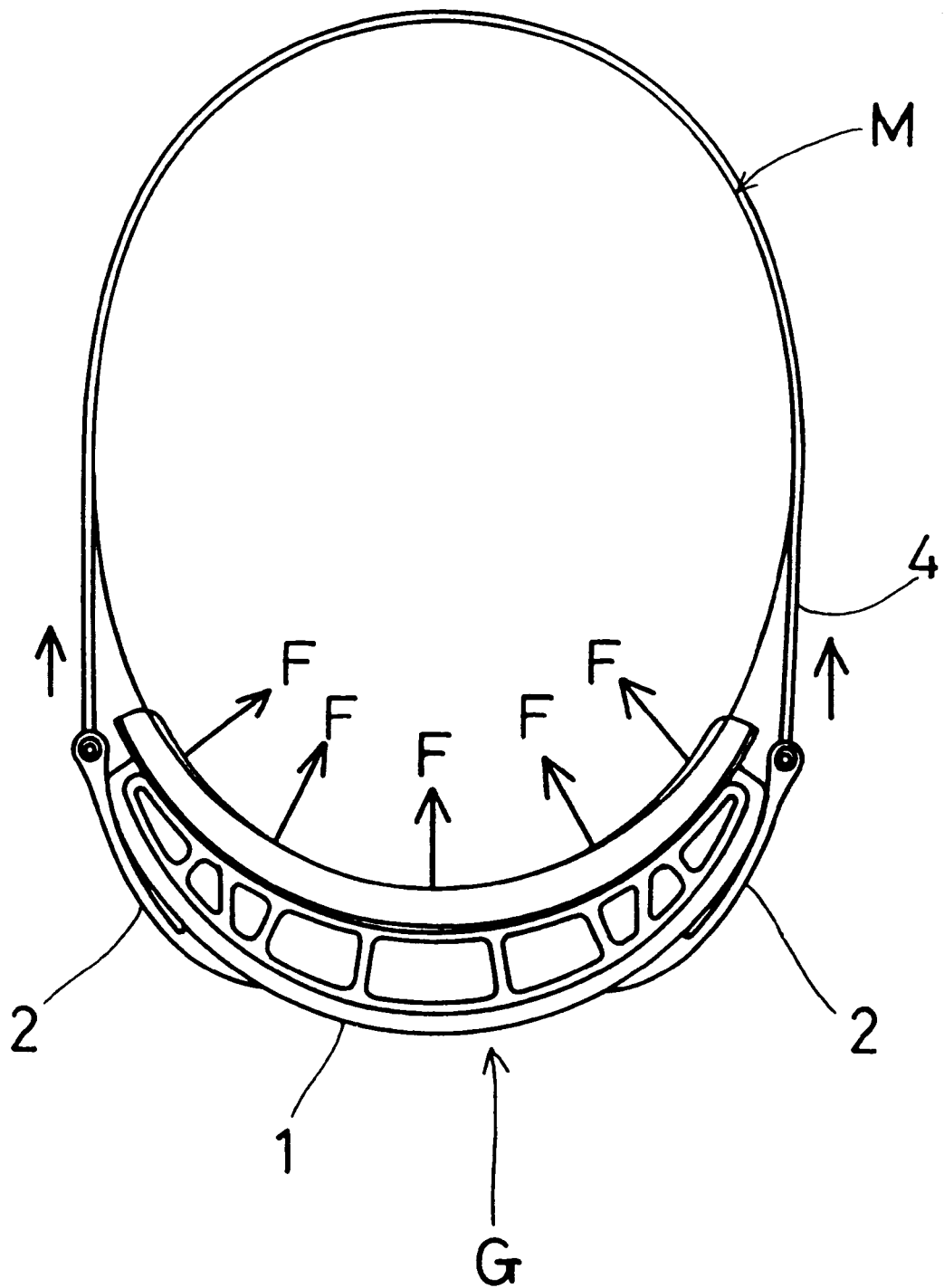
FIG. 8 is a cross section showing a state where the goggles are put directly on a wearer's head.

FIG. 8 shows a state where the goggles are put directly on a wearer's head M. In this case, due to the elastic restoring force of the elastic strap 4, rear surfaces of the arms 2 get closer to and contact the front surface of the frame 1, and additional pressure F from the thus contacting surfaces is further applied on the wearer's face. Therefore, when the goggles G are put directly on the wearer's head, a force will not be exerted on the goggles to rise and separate from the wearer's face.

All of the FIGS. 5 to 8 show the goggles having the protrusion positions of the arms 2 on the front surface of the lens holding frame, however, the upper protrusion positions may be disposed on a top surface of the lens holding frame 10. In the latter case, a similar effect can be also obtained as long as the arms 2 extend along the front surface of the lens holding frame 10. However, when the latter type of helmet is used, there exists a gap corresponding to the size of the protrusion of the arms 2 exists between the helmet and the goggles. Consequently, it is more preferable to have the protrusion positions on the front surface of the lens holding frame 10.

As stated above, when the goggles G according to the present invention are used, a wide view can always be secured whether a helmet is used or not, or regardless of the thickness of the interior liner R of a helmet, and a wearer can always obtain and feel a desired comfort level. As a result, one can participate in various kinds of races with the one and same model of goggles. In addition, the goggles G in the above embodiments have the arms 2 on the front surface of the frame 1, which can reduce the shock on a wearer's face from the front surface in case of a collision with a pole or the like. Furthermore, since the arms 2 and the frame 1 are integrally made of vinyl chloride the production cost can be reduced because there is no need of assembly and enhancement of design can be readily achieved.

The goggles described above are intended for skiing, but the present invention can also be adapted to various types of goggles for other sports and recreational activities such as motocross or for work. In these cases, likewise, a wide view can be obtained, a comfortable fit on a user's face can be guaranteed, and intrusion of foreign materials such as snow and dust can be prevented.

Figure 9:
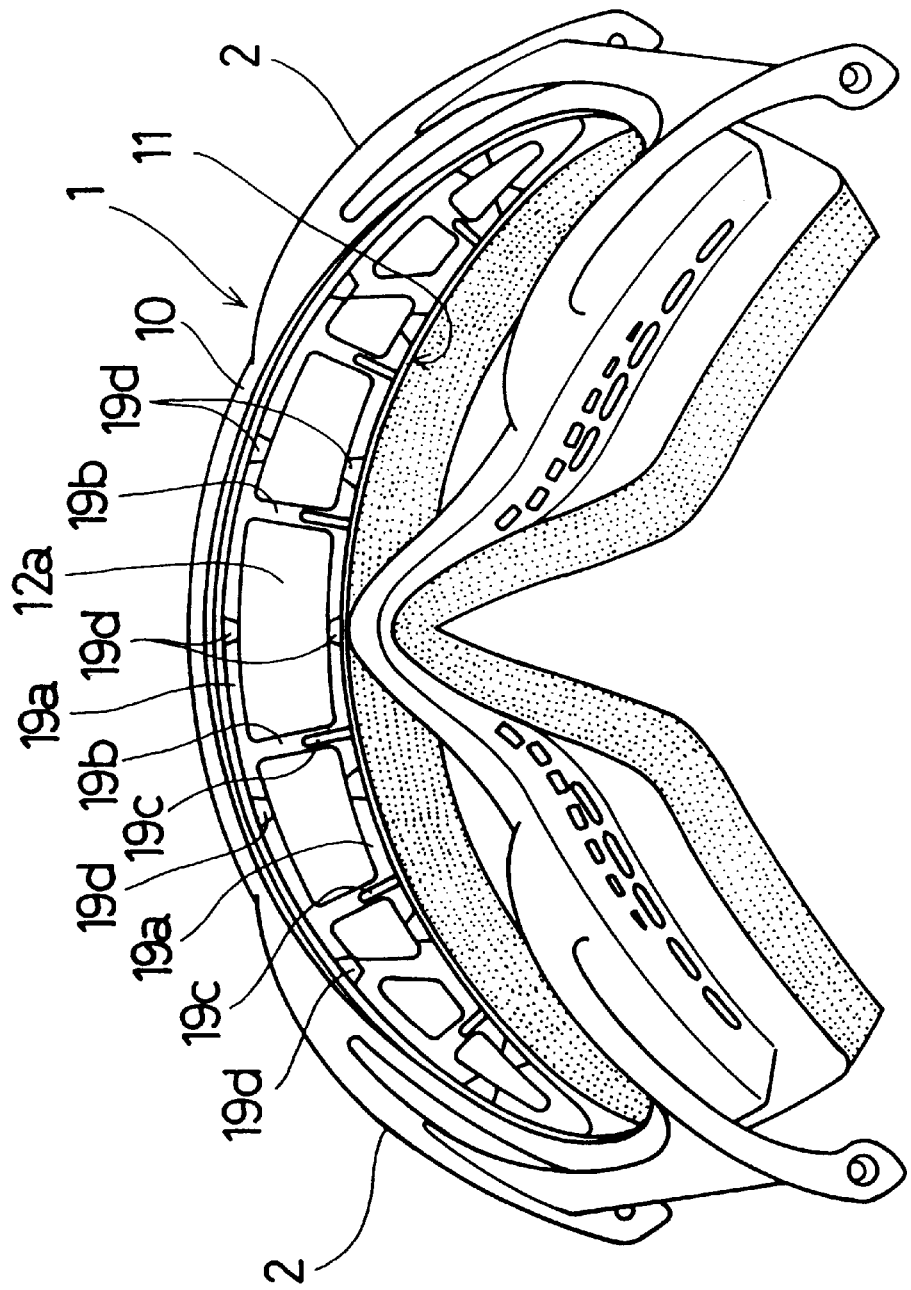
FIG. 9 is a view showing an interior of an upper ventilation part of a pair of goggles according to another embodiment of the present invention.
Figure 10:
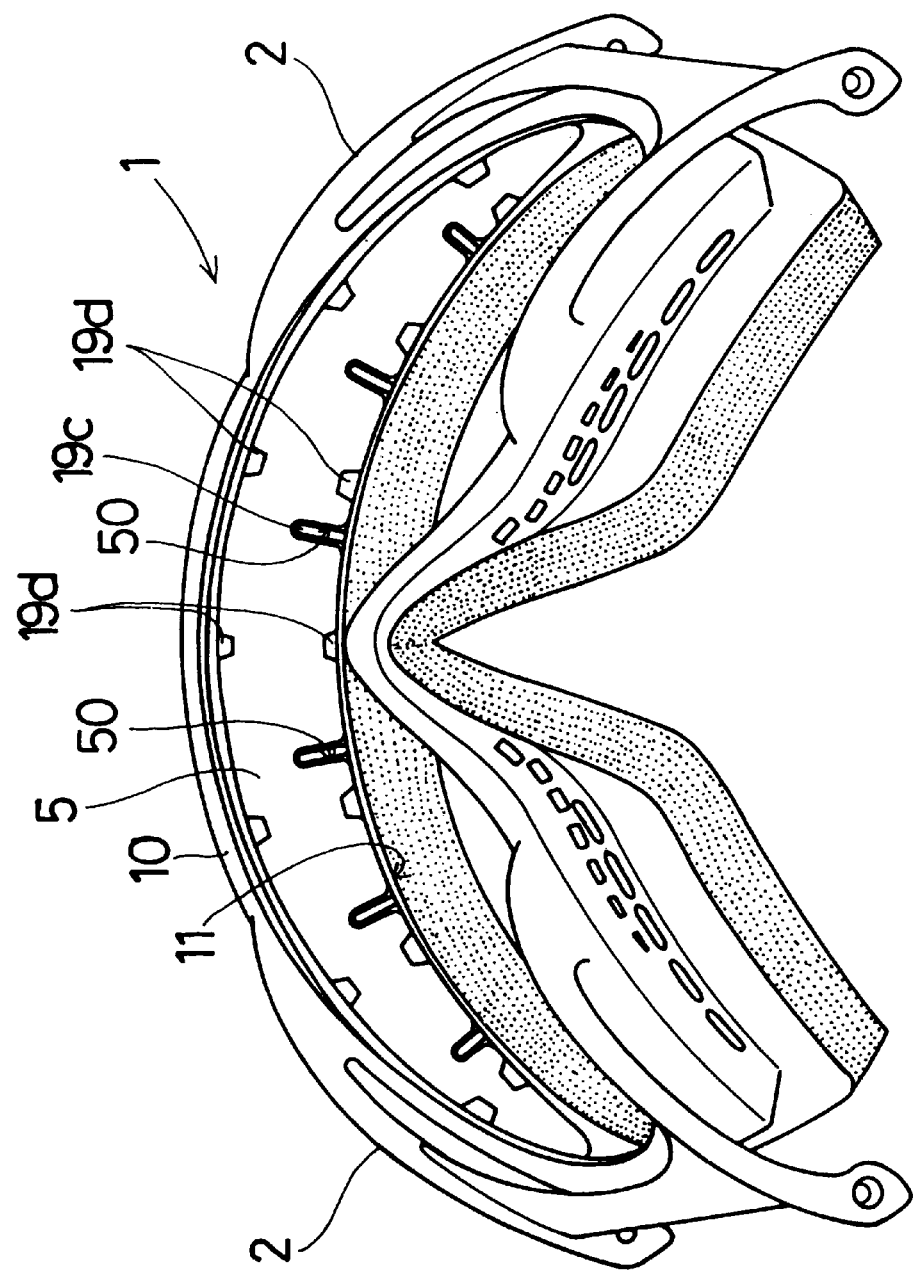
FIG. 10 is a view showing a state where a wind shielding plate is put in place under the ventilation part.
Figure 11:
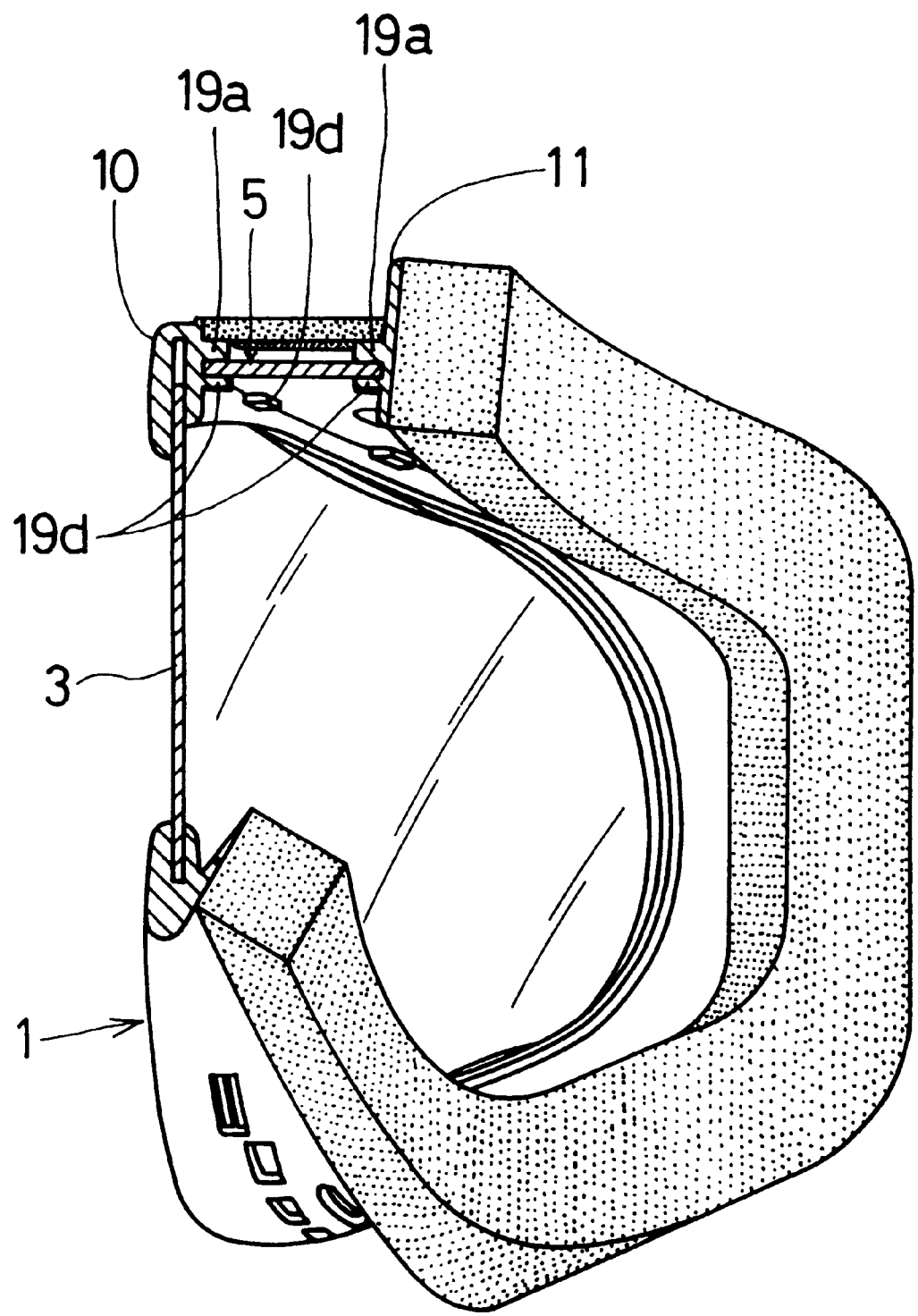
FIG. 11 is a vertical cross section of FIG. 10.
Figure 12:
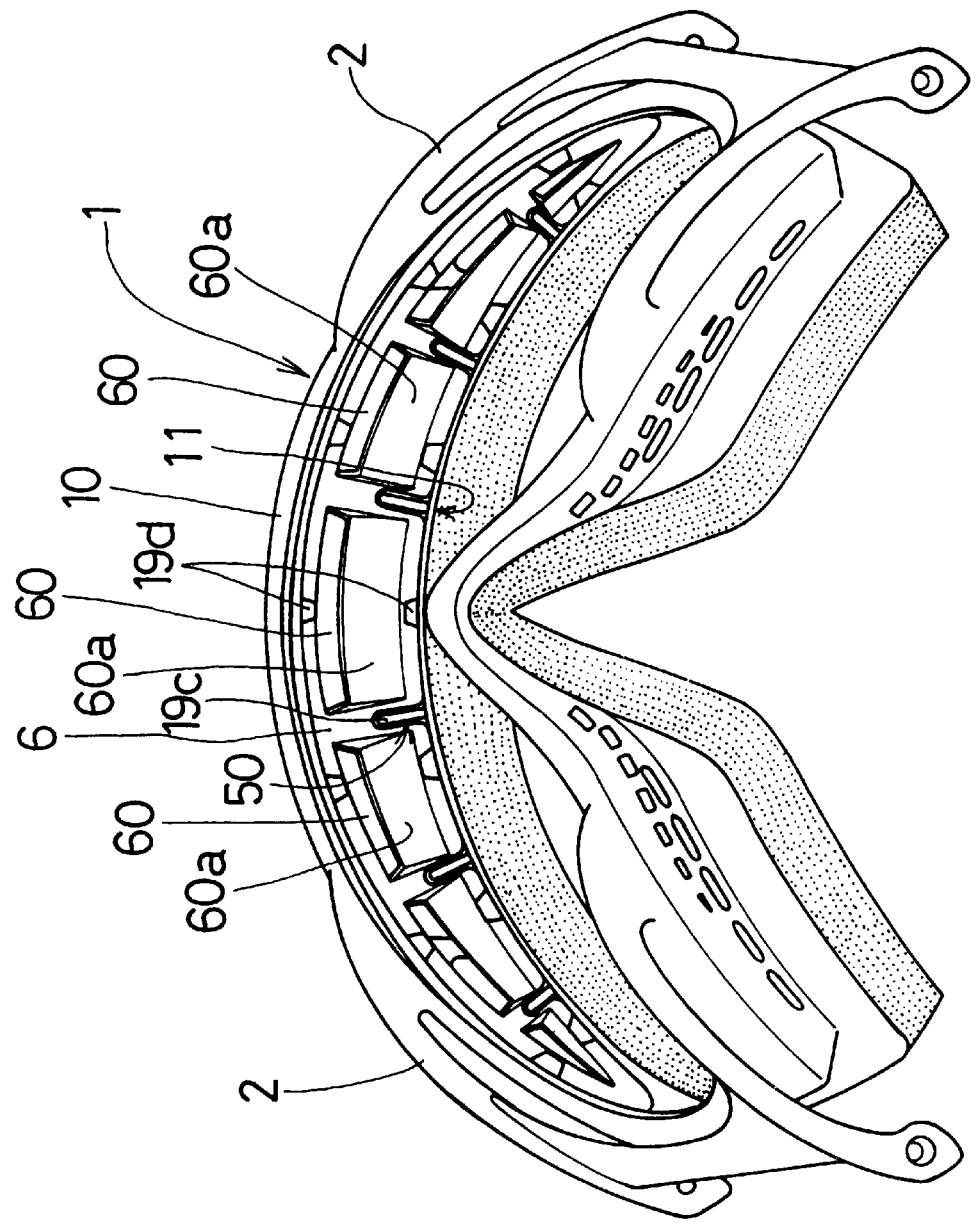
FIG. 12 is a view showing a state where a wind shifting plate is put in place under the ventilation part.
Figure 13:
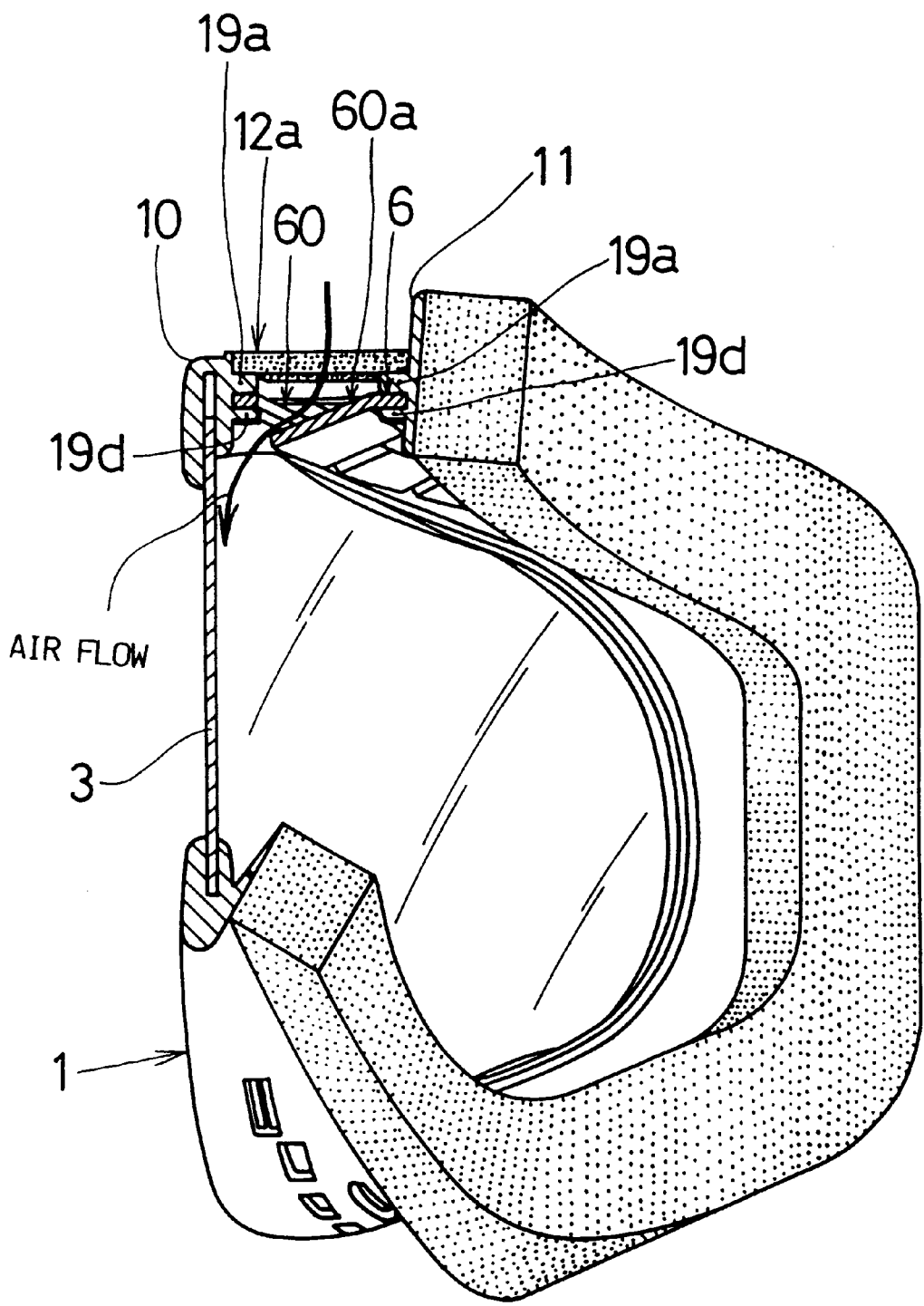
FIG. 13 is a vertical cross section of FIG. 12.
Figure 14:
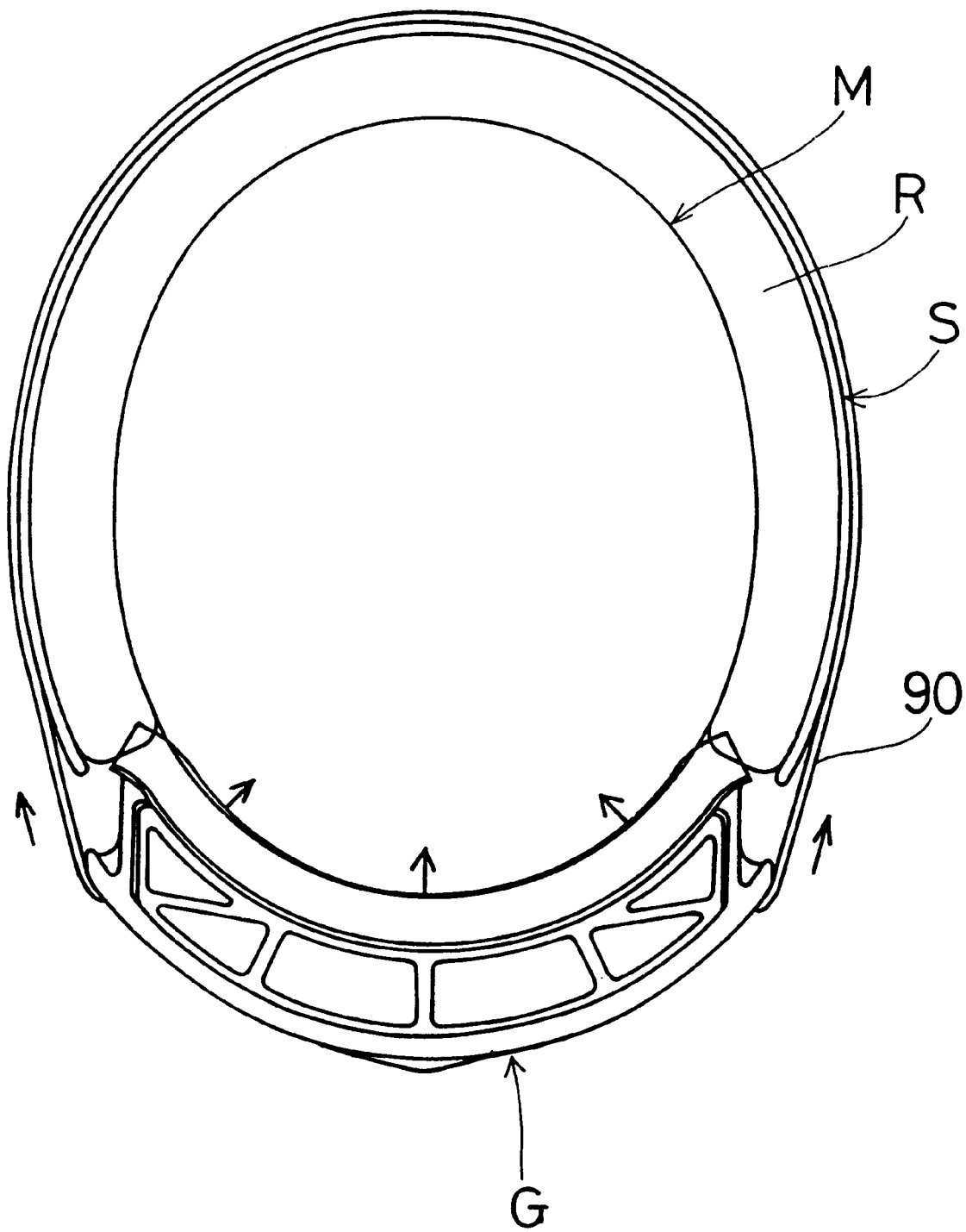
FIG. 14 is a cross section showing a state where a conventional pair of goggles are put on a helmet with a thick interior liner.
Figure 15:
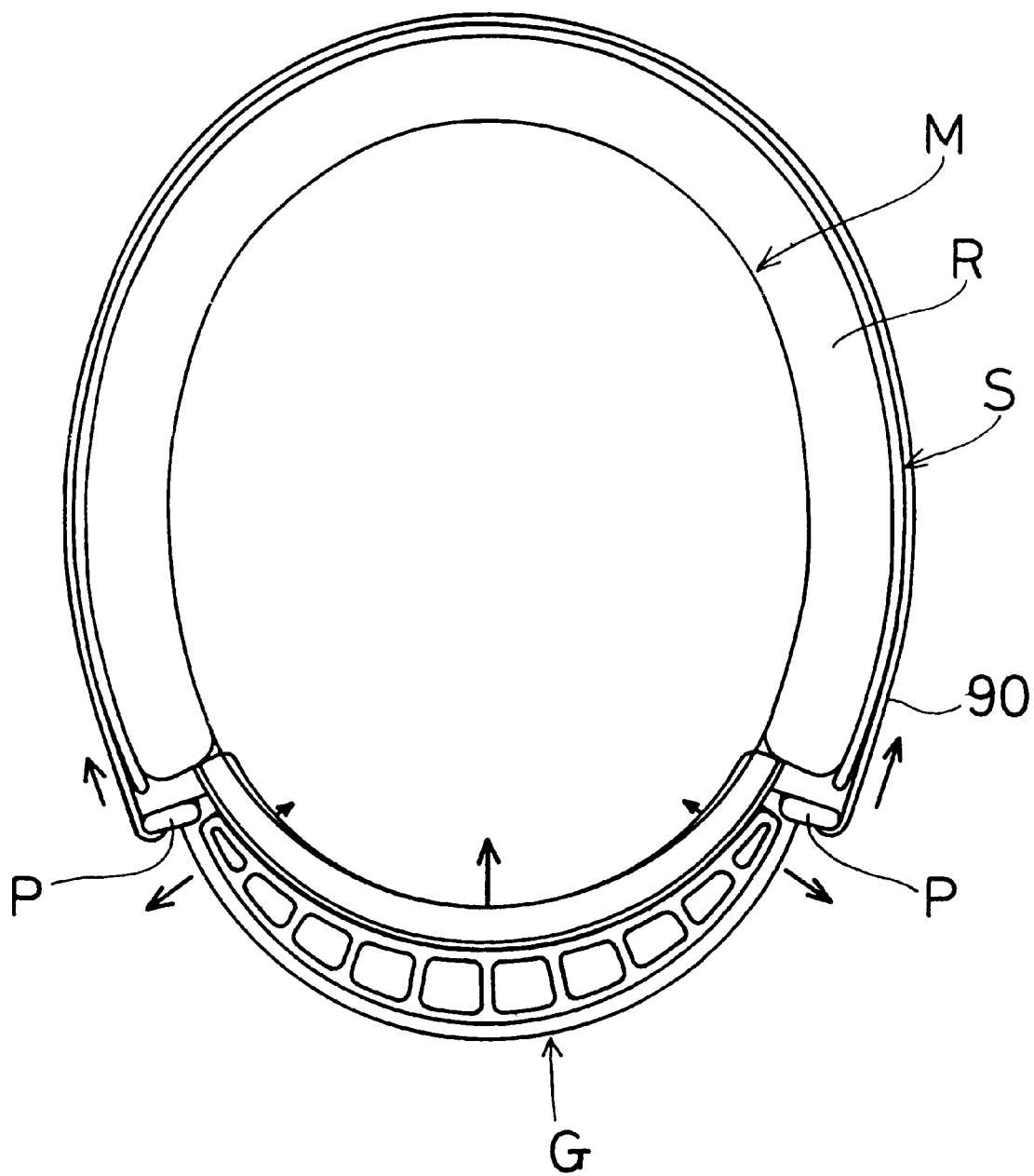
FIG. 15 is a cross section showing a state where another conventional pair of goggles are put on a helmet with a thick interior liner.

FIG. 9 shows another embodiment. The frame 1 of the goggles is designed to detachably receive a wind shielding plate 5 or a wind shifting plate 6 inside the ventilation part 12a. FIGS. 10 and 11 show a state where the wind shielding plate 5 is provided therein, while FIGS. 12 and 13 show a state where the wind shifting plate 6 is provided therein.

This frame 1, as shown in FIG. 9, includes reception bars 19a respectively on the backside of the lens holding frame 10 and the front-side of the base plate 11, and a plurality of connection bars 19b to bridge the space between the reception bars 19a, which define the ventilation part 12a. A plurality of positioning pieces 19c extend from the front side of the base plate 11 to under and along the connection bars 19b. Additionally referring to FIG. 11, small tongues 19d are provided respectively on the backside of the lens holding frame 10 and on the front side of the base plate 11 with a small space from the reception bars 19a to receive the wind shielding plate 5 or the wind shifting plate 6. The space corresponds to the thickness of the edge portion of the wind shielding plate 5 or the wind shifting plate 6.

The wind shielding plate 5 is, as shown in FIGS. 10 and 11, made of a thin resin plate, shaped as a substantially crescent contour in its plane view, and provided with slits 50 at the positions corresponding to the positioning bars 19c on the front-side of the base plate 11. This wind shielding plate 5 is attached to the underside of the ventilation part 12a of the frame 1 in a manner that the positioning pieces 19c are inserted into the slits 50 and the circumferential edge of the plate 5 is inserted between the reception bars 19a and the small tongues 19d.

The wind shifting plate 6 is made similar to the wind shielding plate 5 stated above. Namely, the wind shifting plate 6 is made of a thin resin plate, and has a crescent contour in its plane view. The plate 6 further includes slits 50 at the positions corresponding to those of the positioning bars 19c, and is put in place under the ventilation part 12a by engaging with the positioning bars 19c, the reception bars 19a and the small tongues 19d. However, as shown in FIGS. 12 and 13, the wind shifting plate 6 is further provided with an air guide path 60 which is defined by a slant plate 60a. This plate 60a inclines downwardly ahead so as to let air coming in from the ventilation part 12a flow down along the lens 3.

Constituted as stated above, the present invention can provide a pair of goggles which give a comfortable fit on a wearer's face whether used with or without a helmet or regardless of thickness of the interior liner of a helmet.

What is claimed is:

1. A pair of goggles comprising:

a frame of soft elastic synthetic resin having at least an upper frame portion and a lower frame portion;

arms of soft elastic synthetic resin integrally formed with said frame and respectively extending from associated extrusion positions on said upper and lower frame portions, said associated extrusion positions being set at positions between a center position and lateral end positions of said frame, said arms extending generally rearwards for some length along said frame and being provided with strap attaching positions at distal end portions located away from said extrusion positions; and a strap attached to said strap attaching portions by a strap attaching means.

2. A pair of goggles according to claim 1, wherein said frame further comprises a lens holding frame in front, a base plate behind said lens holding frame, a thick sponge pad behind said base plate, and a ventilation part between said lens holding frame and said base plate.

3. A pair of goggles according to claim 2, wherein a wind shielding plate is detachably provided under said ventilation part.

4. A pair of goggles according to claim 2, wherein a wind shifting plate is detachably provided under said ventilation part.

5. A pair of goggles according to claim 1, wherein a distance between one of said protrusion positions and the center of said lens holding frame is 2 to 8 cm.

6. A pair of goggles according to claim 1, wherein said associated extrusion positions are located on a top and a bottom surface of said frame and said arms extend overlapping with at least part of a front surface of said frame.

7. A pair of goggles according to claim 1, wherein said associated extrusion positions are located on a front surface of said frame and said arms extend generally along said front surface.

8. A pair of goggles according to claim 2, wherein said associated extrusion positions are located on a top and a bottom surface of said lens holding frame, and said arms extend overlapping with at least part of a front surface of said lens holding frame.

9. A pair of goggles according to claim 2, wherein said associated extrusion positions are located on a front surface of said lens holding frame, and said arms extend generally along said front surface of said lens holding frame.

10. A pair of goggles according to claim 1, wherein said arms extruding rearwards from said upper and lower frame portions are connected with an arm-bridging part having a shape corresponding to a configuration of a front surface of each lateral end portion of said frame.

11. A pair of goggles according to claim 2, wherein said arms extruding from said lens holding frame are connected with an arm-bridging part with a shape corresponding to a configuration of a front surface of each lateral end portion of said lens holding frame.

12. A pair of goggles according to claim 1, wherein said frame is gradually thinner towards each of said lateral end positions.

* * * * *